(12) United States Patent
Mistretta et al.

(10) Patent No.: US 8,823,704 B2
(45) Date of Patent: *Sep. 2, 2014

(54) SYSTEM AND METHOD OF TIME-RESOLVED, THREE-DIMENSIONAL ANGIOGRAPHY

(71) Applicants: Mistretta Medical, LLC, Madison, WI (US); CMS Medical, LLC, Madison, WI (US)

(72) Inventors: Charles A. Mistretta, Madison, WI (US); Charles M. Strother, Madison, WI (US)

(73) Assignees: Mistretta Medical, LLC, Madison, WI (US); CMS Medical, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/135,259

(22) Filed: Dec. 19, 2013

(65) Prior Publication Data

US 2014/0142423 A1    May 22, 2014

Related U.S. Application Data

(63) Continuation of application No. 12/542,376, filed on Aug. 17, 2009, now Pat. No. 8,643,642.

(51) Int. Cl.
| | |
|---|---|
| *G06T 15/00* | (2011.01) |
| *A61B 6/00* | (2006.01) |
| *H05G 1/60* | (2006.01) |
| *A61M 5/00* | (2006.01) |
| *A61B 6/12* | (2006.01) |

(52) U.S. Cl.
CPC .............. *A61B 6/5235* (2013.01); *A61M 5/007* (2013.01); *A61B 6/12* (2013.01); *A61B 6/4441* (2013.01); *A61B 6/485* (2013.01); *A61B 6/487* (2013.01); *A61B 6/481* (2013.01); *Y10S 378/901* (2013.01)
USPC .................... 345/419; 378/4; 378/901; 378/9

(58) Field of Classification Search
None
See application file for complete search history.

(56) References Cited

U.S. PATENT DOCUMENTS

| 4,482,918 A | 11/1984 | Keyes et al. |
| 6,317,621 B1 | 11/2001 | Graumann et al. |

(Continued)

FOREIGN PATENT DOCUMENTS

WO    WO-2006/106470    10/2006

OTHER PUBLICATIONS

Dumay et al. "Developments towards slice-wise three-dimensional reconstruction of the distribution of the contrast perfusion in the myocardial muscle from biplane angiographic view." International Journal of Cardiac Imaging 5, 1990, pp. 213-224.

(Continued)

*Primary Examiner* — Kee M Tung
*Assistant Examiner* — Zhengxi Liu
(74) *Attorney, Agent, or Firm* — Foley & Lardner LLP

(57) ABSTRACT

A method for generating time-resolved 3D medical images of a subject by imparting temporal information from a time-series of 2D medical images into 3D images of the subject. Generally speaking, this is achieved by acquired image data using a medical imaging system, generating a time-series of 2D images of a ROI from at least a portion of the acquired image data, reconstructing a 3D image substantially without temporal resolution from the acquired image data, and selectively combining the time series of 2D images with the 3D image. Selective combination typically involves registering frames of the time-series of 2D images with the 3D image, projecting pixel values from the 2D image frames "into" the 3D image, and weighting the 3D image with the projected pixel values for each frame of the time-series of 2D images. This method is particularly useful for generating 4D-DSA images, that is, time-resolved 3D-DSA images, from a time-series of 2D-DSA images acquired via single plane or biplane x-ray acquisitions with 3D images acquired via a rotational DSA acquisition. 4D-DSA images can also be generated by selectively combining a time-series of 2D-DSA images generated from individual projections from a rotational x-ray acquisition with a 3D image reconstructed from substantially all of the projection views acquired during the rotational x-ray acquisition. These DSA images may have a spatial resolution on the order of $512^3$ pixels and a temporal resolution of about 30 frames per second, which represents an increase over traditional 3D-DSA frame rates by a factor between 150 and 600.

20 Claims, 9 Drawing Sheets

(56) References Cited

U.S. PATENT DOCUMENTS

| | | |
|---|---|---|
| 6,823,204 B2 | 11/2004 | Grass et al. |
| 6,983,182 B2 | 1/2006 | Mistretta |
| 7,020,314 B1 | 3/2006 | Suri et al. |
| 7,054,405 B2 | 5/2006 | Edic et al. |
| 7,305,062 B2 | 12/2007 | Hambuchen et al. |
| 7,545,901 B2 | 6/2009 | Mistretta |
| 7,590,442 B2 | 9/2009 | Boese et al. |
| 7,738,626 B2 | 6/2010 | Weese et al. |
| 8,009,885 B2 | 8/2011 | Grass et al. |
| 8,285,360 B2 | 10/2012 | Kabasawa |
| 2001/0007593 A1 | 7/2001 | Oosawa |
| 2004/0116812 A1 | 6/2004 | Selzer et al. |
| 2005/0080328 A1 | 4/2005 | Vass et al. |
| 2005/0084060 A1 | 4/2005 | Seppi et al. |
| 2005/0232389 A1 | 10/2005 | Klingenbeck-Regn |
| 2006/0165213 A1 | 7/2006 | Hambuchen et al. |
| 2006/0173297 A1 | 8/2006 | Popescu |
| 2006/0250386 A1 | 11/2006 | Movassaghi et al. |
| 2007/0009080 A1 | 1/2007 | Mistretta |
| 2007/0055148 A1 | 3/2007 | Klingenbeck-Regn |
| 2007/0183569 A1 | 8/2007 | Boese et al. |
| 2008/0051648 A1 | 2/2008 | Suri et al. |
| 2008/0192997 A1 | 8/2008 | Grass et al. |
| 2008/0212857 A1 | 9/2008 | Pfister et al. |
| 2008/0243435 A1 | 10/2008 | Deinzer et al. |
| 2008/0300478 A1 | 12/2008 | Zuhars et al. |
| 2008/0304728 A1 | 12/2008 | Licato et al. |
| 2009/0010380 A1 | 1/2009 | Gotoh |
| 2009/0074277 A1 | 3/2009 | Deinzer et al. |
| 2009/0088830 A1 | 4/2009 | Mohamed et al. |
| 2009/0093712 A1 | 4/2009 | Busch et al. |
| 2010/0053209 A1 | 3/2010 | Rauch et al. |
| 2010/0061611 A1 | 3/2010 | Xu et al. |
| 2010/0201786 A1 | 8/2010 | Schaefer et al. |
| 2010/0296623 A1 | 11/2010 | Mielekamp et al. |
| 2011/0037761 A1 | 2/2011 | Mistretta et al. |
| 2011/0038517 A1 | 2/2011 | Mistretta et al. |
| 2013/0039559 A1 | 2/2013 | Grass et al. |
| 2013/0123611 A1 | 5/2013 | Riederer et al. |

OTHER PUBLICATIONS

Chen et al., "Blood Flow Measurement by Cone-Beam CT Bolus Imaging", Proceedings of the SPIE, vol. 6143, 61432J, 2006, 12 pages.

International Search Report and Written Opinion for PCT Application No. PCT/US2010/045637, mailed Apr. 12, 2011, 7 pages.

International Search Report and Written Opinion for PCT Application No. PCT/US2011/022120, mail date Aug. 26, 2011, 9 pages.

International Search Report and Written Opinion for PCT Application No. PCT/US2012/042491, mailed Mar. 4, 2013, 10 pages.

Kohler et al., "Method for Flow Reconstruction from Dynamic X-Ray Projection Measurements", Nuclear Science Symposium Conference Record, 2004 IEEE, vol. 5, Oct. 2004, 4 pages.

Lessard et al., "Automatically Driven Vector for Line Segmentation in 2D and Biplane Imaging Modality", 15 International Conference of Image Analysis and Processing, Italy, Sep. 8-11, 2009, 9 pages.

Liu et al., "Renal Perfusion and Hemodynamics: Accurate in Vivo Determination at CT with a 10-Fold Decrease in Radiation Dose and HYPR Noise Reduction", Radiology, vol. 253, No. 1, Oct. 2009, 8 pages.

Mistretta et al., "HYPR: Constrained Reconstruction for Enhanced SNR in Dynamic Medical Imaging", Medical Imaging 2008: Physics of Medical Imaging, Proceedings of the SPIE, vol. 6913, 2008, 9 pages.

Nth Root, http://www.mathisfun.com/numbers/nth-root.html, Archived on Dec. 21, 2007, Retrieved Jul. 10, 2012 from http://web.archive.org/web/20071221121146/http://www.mathisfun.com/numbers/nth-root.html, 6 pages.

Office Action for U.S. Appl. No. 12/542,376, mail date Aug. 16, 2012, 54 pages.

Pollmann et al., "Four Dimensional Intravenous Cone-Beam Computed Tomographic Subtraction Angiography", Investigative Radiology, vol. 43, No. 11, Nov. 2008, 9 pages.

Schmitt et al., "An X-Ray-Based Method for the Determination of the Contrast Agent Propagation in 3-D Vessel Structures", IEEE Transactions on Medical Imaging, vol. 21, No. 3, Mar. 2002, 12 pages.

Schmitt et al., "Reconstruction of Blood Propagation in Three-Dimensional Rotational X-ray Angiography (3D-RA)", Computerized Medical Imaging and Graphics, vol. 29, Issue 7, Oct. 2005, 14 pages.

Waechter et al., "Using Flow Information to Support 3D Vessel Reconstruction from Rotational Angiography", Med. Phys. 35 (7), Jul. 2008, 15 pages.

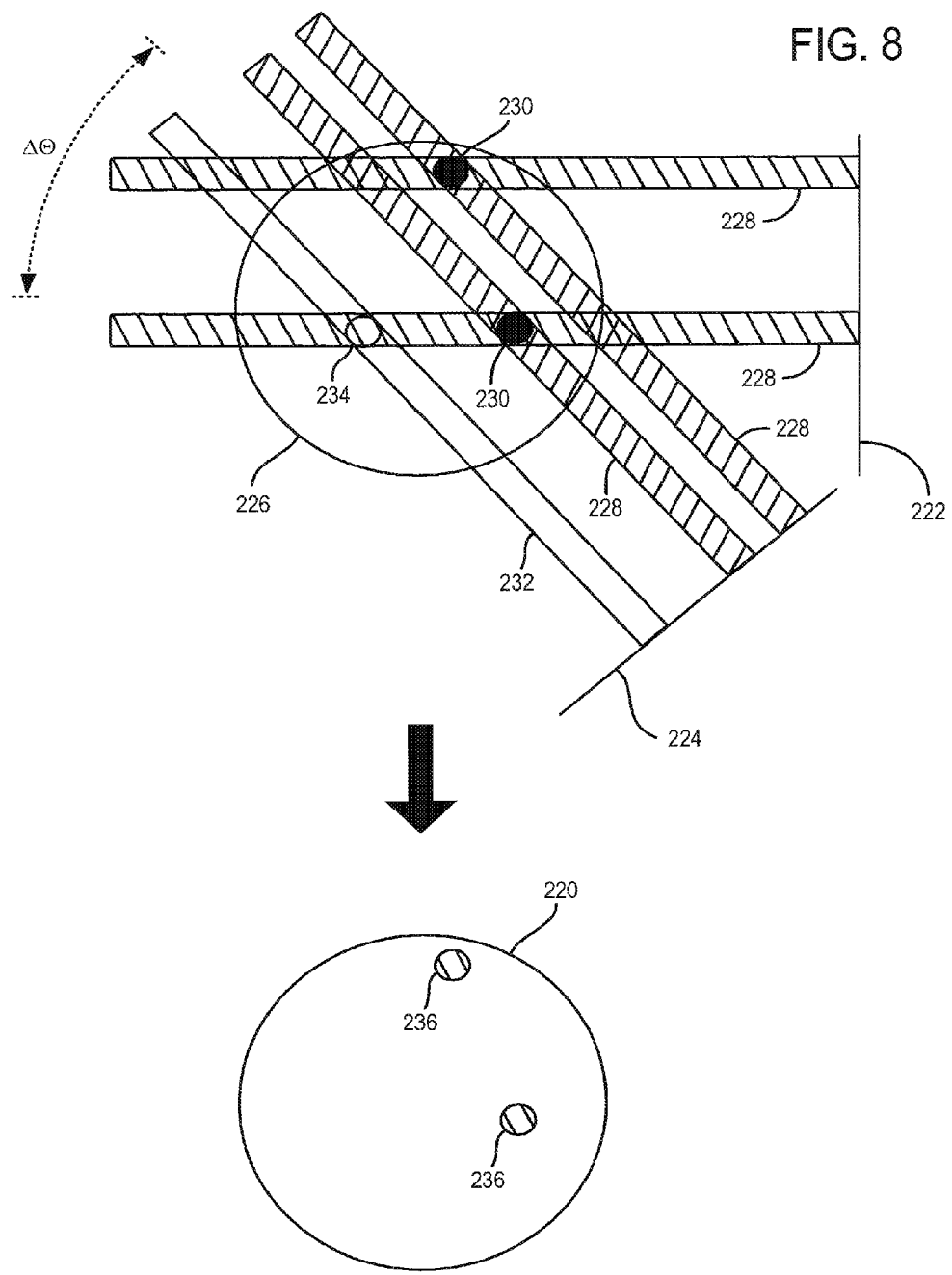

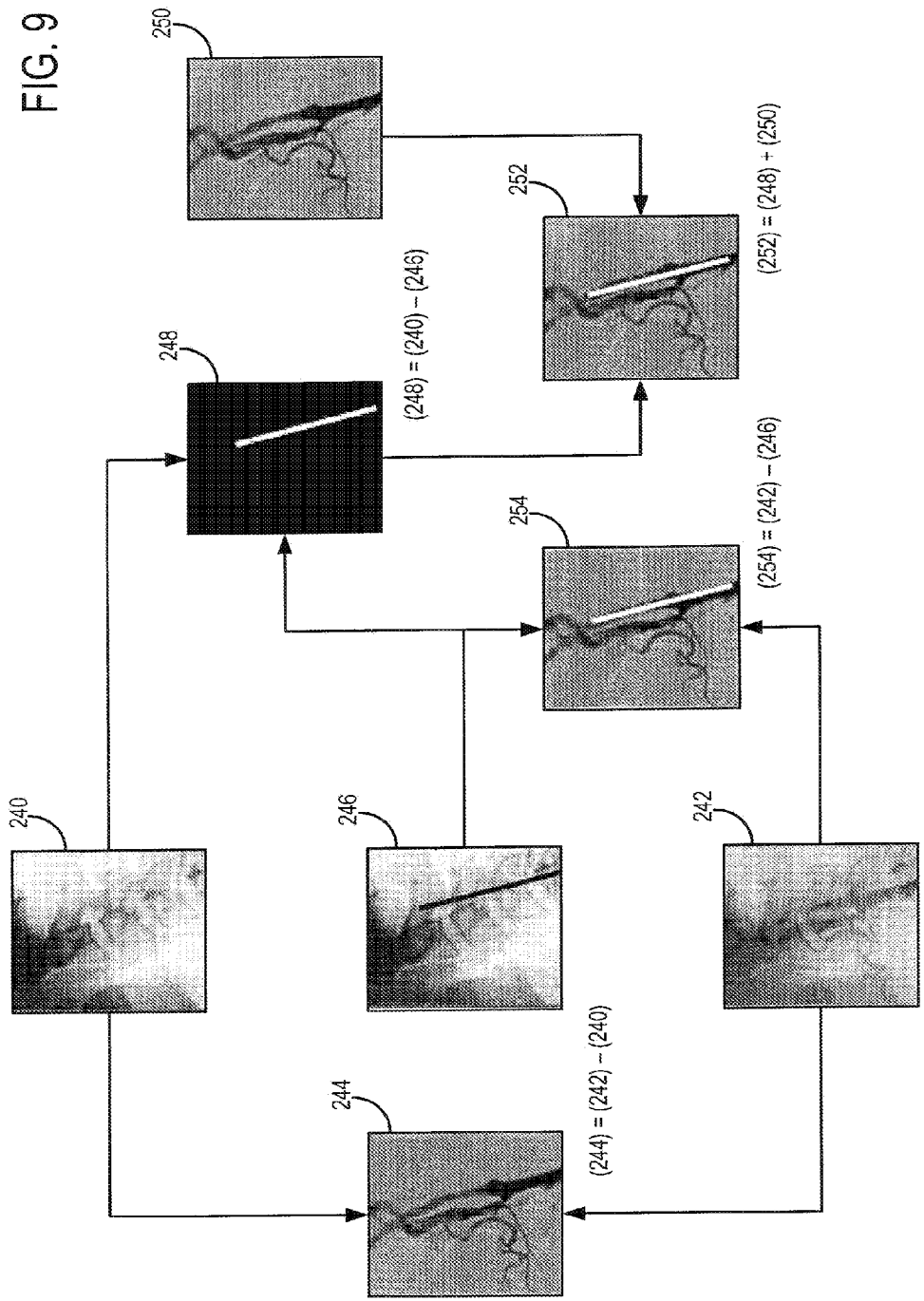

SYSTEM AND METHOD OF TIME-RESOLVED, THREE-DIMENSIONAL ANGIOGRAPHY

CROSS-REFERENCE TO RELATED APPLICATIONS

This application is a continuation of U.S. application Ser. No. 12/542,376, filed Aug. 17, 2009, which is incorporated herein by reference in its entirety.

BACKGROUND OF THE INVENTION

The present invention is related to angiography and, in particular, the invention relates to a system and method for producing time-resolved, three-dimensional (3D) angiographic images.

Since the introduction of angiography beginning with the direct carotid artery punctures of Moniz in 1927, there have been ongoing attempts to develop angiographic techniques that provide diagnostic images of the vasculature, while simultaneously reducing the invasiveness associated with the procedure. For decades, post-processing of images was largely limited to the use of film subtraction techniques. Initial angiographic techniques involved direct arterial punctures and the manipulation of a needle through which a contrast medium was injected. These practices were associated with a significant incidence of serious complications. The development of percutaneous techniques allowing the use of a single catheter to study multiple arterial segments reduced, but this by no means eliminated, these adverse events. In the late 1970's, a technique known as digital subtraction angiography (DSA) was developed based on real-time digital processing equipment. Because of the advantages of digital processing, it was originally hoped that DSA could be consistently implemented using an IV injection of contrast medium, thus reducing both the discomfort and the incidence of complications associated with direct IA injections.

However, it quickly became apparent that the IV-DSA technique was limited by problems due to suboptimal viewing angles and vessel overlap that could only be reduced by repeated injections. Even then, these factors were problematic unless a projection that avoided the overlap of relevant vascular structures could be defined. Similar problems occurred when using biplane acquisitions. Also, because of the limited amount of signal associated with the IV injection of contrast medium, IV-DSA was best performed in conditions with adequate cardiac output and minimal patient motion. IV-DSA was consequently replaced by techniques that combined similar digital processing with standard IA angiographic examinations. Nevertheless, because DSA can significantly reduce both the time necessary to perform an angiographic examination and the amount of contrast medium that was required, its availability resulted in a significant reduction in the adverse events associated with angiography. Due to steady advancements in both hardware and software, DSA can now provide exquisite depictions of the vasculature in both 2D and rotational 3D formats. Three-dimensional digital subtraction angiography (3D-DSA) has become an important component in the diagnosis and management of people with a large variety of central nervous system vascular diseases.

Current limitations in the temporal resolution capabilities of x-ray angiographic equipment require that rotational acquisitions be obtained over a minimum time of about 5 seconds. Even with perfect timing of an acquisition so that arterial structures are fully opacified at the onset of a rotation, there is almost always some filling of venous structures by the end of the rotation. Display of a "pure" image of arterial anatomy is only achieved by thresholding such that venous structures, which contain lower concentrations of contrast medium than arterial structures, are no longer apparent in the image. This limitation is a significant factor in making it prohibitively difficult to accurately measure the dimensions of both normal and abnormal vascular structures. Current DSA-based techniques do not depict the temporal sequence of filling in a reconstructed 3D-DSA volume.

In recent years competition for traditional DSA has emerged in the form of CT angiography (CTA) and Magnetic Resonance Angiography (MRA). CTA provides high spatial resolution, but is not time-resolved unless the imaging volume is severely limited. CTA is also limited as a standalone diagnostic modality by artifacts caused by bone at the skull base and the contamination of arterial images with opacified venous structures. Further, CTA provides no functionality for guiding or monitoring minimally-invasive endovascular interventions. Significant advances have been made in both the spatial and the temporal resolution qualities of MRA. Currently, gadolinium-enhanced time-resolved MRA (TRICKS) is widely viewed as a dominant clinical standard for time-resolved MRA. TRICKS enables voxel sizes of about 10 $mm^3$ and a temporal resolution of approximately 10 seconds. Advancements such as HYBRID HYPR MRA techniques, which violate the Nyquist theorem by factors approaching 1000, can provide images with sub-millimeter isotropic resolution at frame times just under 1 second. Nonetheless, the spatial and temporal resolution of MRA are not adequate for all imaging situations and its costs are considerable.

Shortcomings of existing angiography methods are particularly prevalent when imaging the small size and convoluted course of the intracranial vasculature. With traditional DSA it is difficult or impossible to image and display these structures without the overlap of adjacent vessels. This problem is compounded when visualizing abnormal structures with complex geometry, such as aneurysms, or when abnormally fast or slow flow is present, such as in vascular malformations or ischemic strokes. As cerebrovascular diseases are increasingly treated using minimally invasive endovascular techniques where a physical is dependent upon imaging techniques for visualization of vascular structures, it is becoming more important to develop imaging methods that allow clear definition of vascular anatomy and flow patterns. Such information is becoming a prerequisite for both pre-treatment planning and the guidance of interventional procedures. For example, the endovascular treatment of vascular disease can require accurate navigation through the small and tortuous vessels of the brain and spinal cord. Currently this involves the use of roadmap that must be "reset" numerous times during a typical procedure. In fact, it is not uncommon to have 15 to 20 resets during a given procedure. Not only does this use large amounts of contrast medium, but the risk of thromboembolic complications increases with each injection.

It would therefore be desirable to have a system and method for producing time-resolved, three-dimensional images of the vasculature with an improved spatial and temporal resolution over those possible currently. The method would allow arterial vasculature to be distinguished from venous vasculature, which would in turn allow the use of IV injections of contrast medium in cases where IA injections are currently performed. This would also allow 3D volumes to be viewed as a dynamic sequence, allowing an improved understanding of vascular diseases and providing a basis for more accurate and versatile roadmaps for use in interventional procedures.

SUMMARY OF THE INVENTION

The present invention overcomes the aforementioned drawbacks by providing a system and method for generating detailed series of time-resolved, three-dimensional medical images of a subject, with both high temporal resolution and excellent spatial resolution, by imparting temporal information from a time-series of 2D images into a still 3D image. This method includes acquiring image data from a subject using a medical imaging system, generating a time-series of two-dimensional images from at least a portion of the acquired image data, and reconstructing a three-dimensional image substantially without temporal resolution from at least a portion of the acquired image data. The method also includes producing a time-resolved three-dimensional image of the subject by selectively combining the three-dimensional image substantially without temporal resolution and the time-series of two-dimensional images.

Another aspect of the present invention includes a method for producing a time-resolved three-dimensional image of a subject by acquiring time-resolved image data from a region-of-interest (ROI) in the subject in a first acquisition performed over a time period during which a bolus of contrast agent passes through the ROI and generating a time-series of two-dimensional images from image data acquired in the first acquisition. The method also includes acquiring image data from the ROI in a second acquisition, reconstructing a three-dimensional image substantially without temporal resolution from the image data acquired in the second acquisition, and producing a time-resolved three-dimensional image of the subject by selectively combing the time-series of two-dimensional images and the three-dimensional image substantially without temporal resolution. In this method, the first acquisition may be performed using a single plane or biplane x-ray system.

In yet another aspect of the present invention, a method is provided for producing a time-resolved three-dimensional image of a subject by acquiring projection views of a region-of-interest (ROI) in the subject over a selected time period using a rotational acquisition, while a bolus of contrast agent passes through the ROI during a portion of the selected time period. The method also includes generating a time-series of two-dimensional images of the ROI from projection views acquired during the portion of the selected time period during which the bolus of contrast agent passes through the ROI. The method further includes reconstructing a three-dimensional image of the ROI substantially without temporal resolution from substantially all of the acquired projection views and producing the time-resolved three-dimensional image of the subject by selectively combining the time-series of two-dimensional images and the three-dimensional image without temporal resolution Various other features of the present invention will be made apparent from the following detailed description and the drawings.

BRIEF DESCRIPTION OF THE DRAWINGS

FIG. 8 schematically depicts the selective combination of a 3D image reconstructed from a full set of projection views with images generated from a pair of individual projection views selected from the set in accordance with the present invention; and FIG. 9 depicts the combination of images involved in generating a 4D fluoroscopic image.

GENERAL DESCRIPTION OF THE INVENTION

Figure 1A:
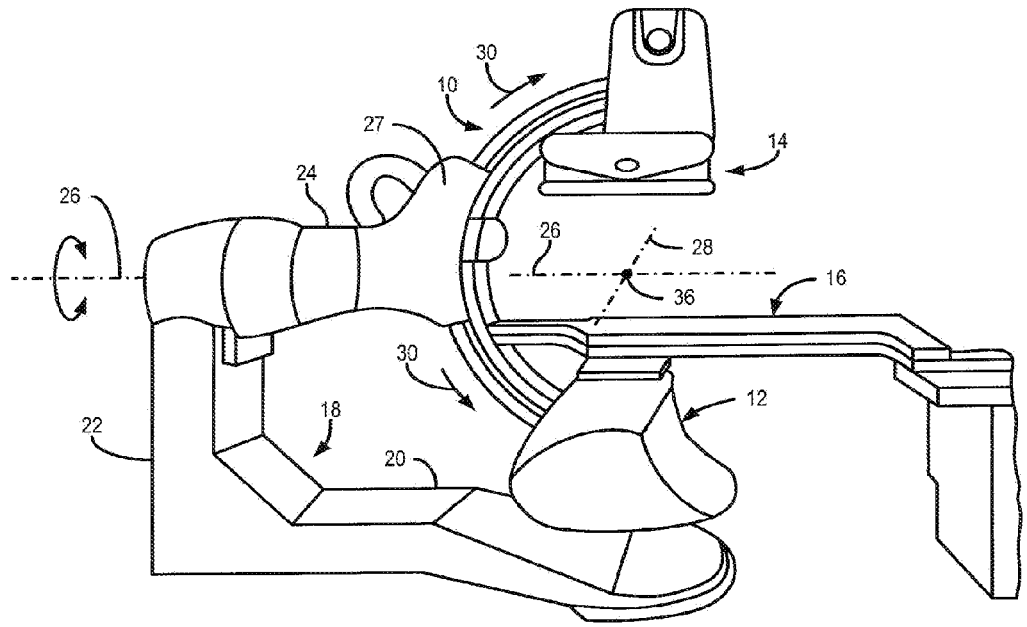
FIGS. 1A and 1B depict a rotational x-ray system configured to carry out a process in accordance with the present invention.

Referring to FIG. 1A, the present invention may employs a rotational x-ray system that is designed specifically for use in connection with interventional procedures. It is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from of the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. The x-ray source 12 emits a beam of x-rays which are directed at the detector array 14. Both assemblies 12 and 14 extend radially inward to the pivot axis 26 such that the center ray of this beam passes through the system isocenter 36. The center ray of the beam can thus be rotated about the system isocenter around either the pivot axis 26 or the C-axis 28, or both during the acquisition of x-ray attenuation data from a subject placed on the table 16.

The x-ray source assembly 12 contains an x-ray source which emits a beam of x-rays when energized. The center ray passes through the system isocenter 36 and impinges on a two-dimensional flat panel digital detector housed in the detector assembly 14. The detector 38 is a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source assembly 12 and detector array assembly 14 are rotated about the system isocenter 36 to acquire x-ray attenuation projection data from different angles. The detector array is able to acquire 30 projections, or views, per second and this is the limiting factor that determines how many views can be acquired for a prescribed scan path and speed.

Figure 1B:
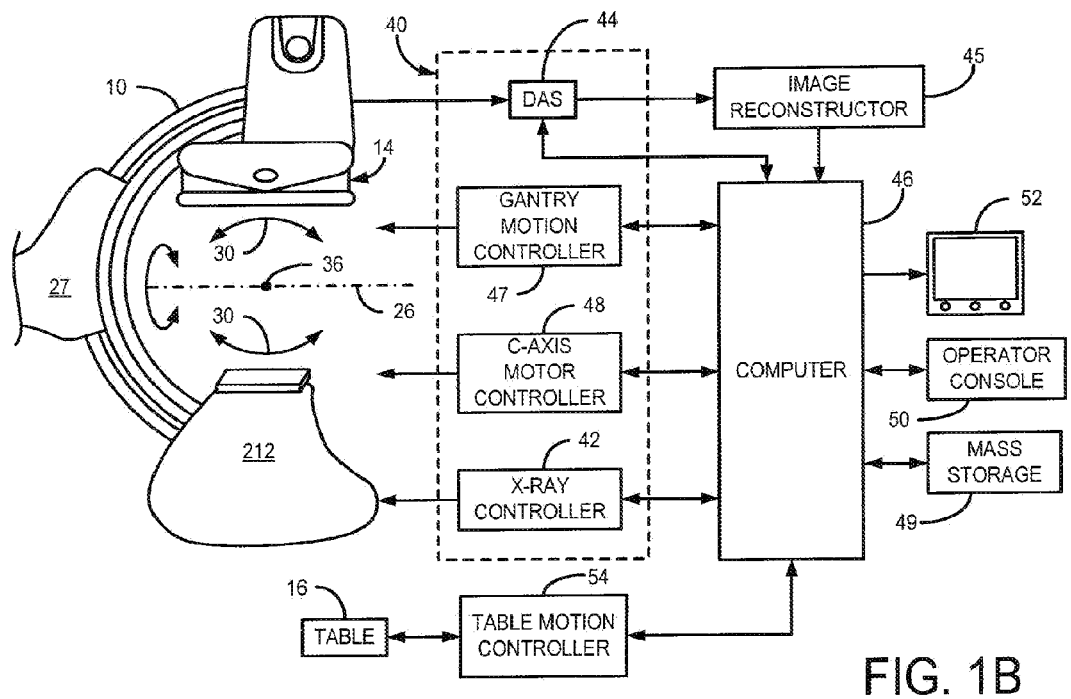

Referring particularly to FIG. 1B, the rotation of the assemblies 12 and 14 and the operation of the x-ray source are governed by a control mechanism 40 of the x-ray system. The control mechanism 40 includes an x-ray controller 42 that provides power and timing signals to the x-ray source 32. A data acquisition system (DAS) 44 in the control mechanism 40 samples data from detector elements 38 and passes the data to an image reconstructor 45. The image reconstructor 45, receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention. It is contemplated that the computer 46 may be or include components of a digital vascular image processor (DVIP) system.

The control mechanism 40 also includes gantry motor controller 47 and a C-axis motor controller 48. In response to motion commands from the computer 46 the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

Whereas conventional reconstruction methods generally necessitate the acquisition of a minimum number of projections dictated by the Nyquist theorem, the present invention provides a fundamentally new method for imparting temporal resolution from a time-series of 2D images into 3D image volumes to create time-resolved 3D medical images. This allows, among other things, the production of 3D angiograms with both exquisite detail and high temporal resolution. The method can be implemented using a wide-variety of medical imaging systems, such as CT systems, fluoroscopy systems, and the above-discussed rotational x-ray system, either alone or in combination. Accordingly, the present description first presents a generalized method for producing time-resolved 3D images before proceeding to more specific implementations and extensions of the method.

Figure 2:
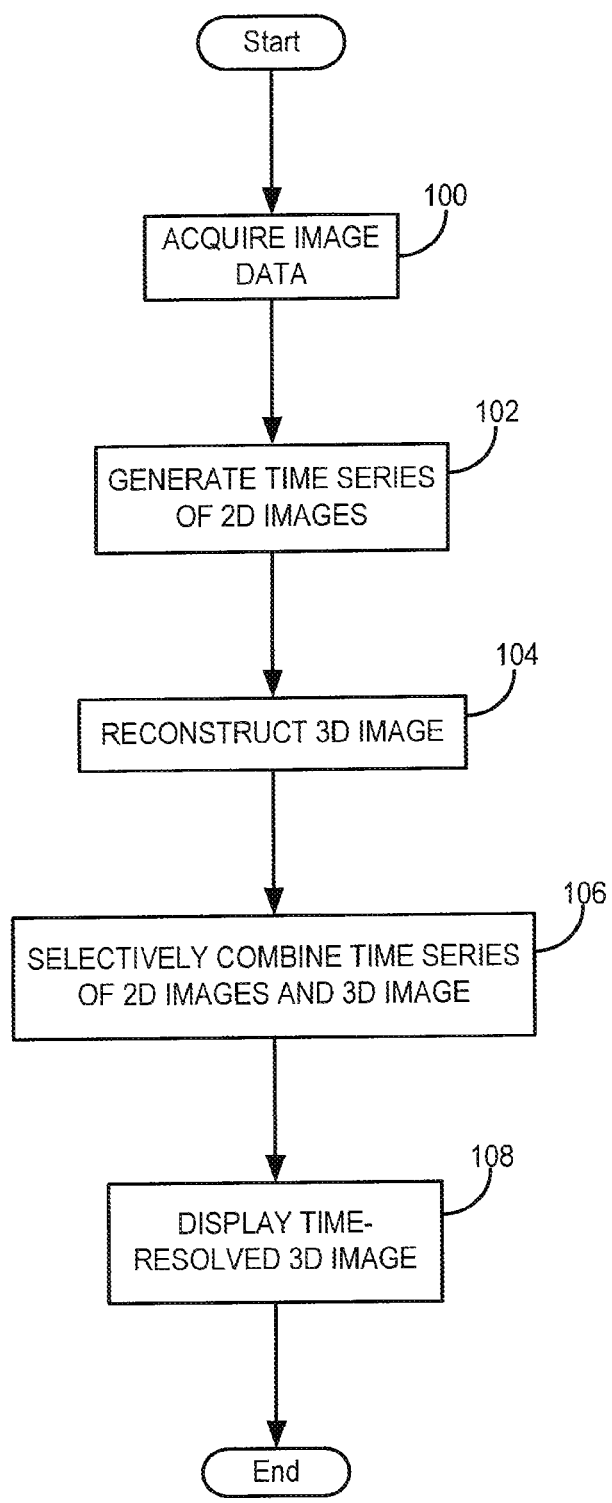
FIG. 2 is a flowchart setting forth the general steps for producing a time-resolved 3D image in accordance with the present invention.

Referring now to FIG. 2, a general method for producing a time-resolved 3D image begins at process block 100 with the acquisition of image data from a region-of-interest in a subject using a medical imaging system, such as a CT system or a single-plane, biplane, or rotational x-ray systems. At process block 102, a time-series of 2D images is generated from at least a portion of the acquired image data. While the time-series of 2D images can have a high temporal and spatial resolution and may include images acquired at different angles around the subject, it generally cannot provide a sophisticated 3D depiction of the subject. The production of the time-series of 2D images may be convolved with a convolution kernel in order to provide local spatial coverage with a desired weighting. For example, these weighted images can provide information detailing how much of a vessel tree is present at a given time. It is contemplated that this process can increase SNR by a factor of three over that provided by the original time series pixels when using a 3×3 convolution kernel. At process block 104, a 3D image of the subject is reconstructed from the acquired image data. Though individual projections used to reconstruct this 3D image may themselves convey some degree of temporal information, the reconstructed 3D image itself is substantially free of temporal resolution. For brevity, the 3D image substantially without temporal resolution and the time-series of 2D images may simply be referred to as the "3D image" and "2D images," respectively. It should be noted that the acquisition and reconstruction of the above sets of image data can be performed in accordance with constrained reconstruction techniques, such as highly constrained backprojection reconstruction (HYPR), to improve SNR and permit potential radiation and contrast agent dose reductions.

At process block 106, the time-series of 2D images and the static 3D image are selectively combined so that the temporal information included in the 2D images is imparted into the 3D image. This results in the production of a time-resolved 3D image of the subject with high temporal and spatial resolution. While the selective combination process varies based on the medical imaging system used and the nature of the acquired image data, it generally involves the steps of (1) registering the 2D images to the 3D image, (2) projecting the attenuation value of the pixels in the 2D images into the 3D image, and (3) weighting the 3D image with the projected values for each individual frame of the time-series of 2D images. It is contemplated that the temporal weighting in step (3) generally involves multiplying the projected pixel values with the 3D image. These three steps, which can be referred to as "multiplicative projection processing" (MPP), may be accompanied by additional steps to improve image quality or reduce the prevalence of errors and artifacts. For example, the intensity values of pixels and voxels in the 2D images and 3D image produced at process blocks 102 and 104 may quantify an x-ray attenuation level at a given location in the subject. These attenuation levels may not be preserved when multiplying the 3D image with projected pixel values. Accordingly, more accurate indications of the attenuation levels may be restored by taking a root of the intensity value at each voxel in the time-resolved 3D image, for example, by taking the n-th root if (n−1) different sets of 2D images are used to weight the 3D image. Other processing steps can be performed before the time-resolved 3D image is displayed at process block 108.

The 2D images and 3D image produced at process blocks 102 and 104, respectively, can be produced using DSA techniques. That is, 2D images depicting the subject's vasculature can be produced by reconstructing image data acquired as a bolus of contrast passes through the ROI and subtracting out a pre-contrast, or "mask," image acquired before the administration of contrast agent. Likewise, a 3D image of the same vasculature can be produced by reconstructing image data acquired as contrast agent occupies the ROI and subtracting out a mask image to remove signal associated with non-vascular structures. As will be discussed below, depending on the imaging situation, the time series of 2D-DSA images and the 3D-DSA images can be produced from image data acquired using a single medical imaging system and contrast agent injection or from different sets of image data acquired separately using different medical imaging systems and contrast agent injections. In either case, the time-resolved 3D image produced by combining the DSA images depicts the subject's vasculature with both excellent spatial and excellent temporal resolution and may thus be referred to as a 4D-DSA image. In additional, the 4D-DSA images can be displayed as "pure" arterial, pure venous, or composite arterial and venous images and can be fully rotated during each state of the filling of the vasculature, thereby enabling greatly simplified interpretation of vascular dynamics. The spatial resolution of these 4D-DSA images is generally on the order of $512^3$ pixels at about 30 frames per second. This represents an increase over traditional 3D-DSA frame rates by a factor between 150 and 600, without any significant image quality penalty being incurred.

The acquisition of contrast enhanced image data can be performed following the administration of contrast agent to the subject via either IV or IA injection. When scanning a local area, IA injections allow high image quality and temporal resolution as well as reduced contrast agent dose. However, IV injections are often more suitable for scanning larger regions where multiple IA injections at different locations and different arteries would otherwise be required. For example, there are many clinical cases where multiple 3D-DSA acquisitions, each using a different IA injection, are performed to produce separate studies that can be merged into a larger high quality vascular tree. While separate IA acquisitions may be employed for generating the time-series of 2D images used by the present invention for temporal weighting, the use of an intravenous injection for this purpose provides a mechanism for simultaneously synchronized imparting temporal information to all of the previously acquired anatomical locations present in instances when there are multiple, separate, IA 3D-DSA studies. This process reduces the likelihood of complications associated with IA contrast agent injections and improves scan efficiency. Further, there is filling of arteries and veins with the same concentration of contrast medium in scans performed using IV rather than an IA contrast agent injections, thus allowing the visualization of venous and arterial structures at the same threshold.

Figure 3:
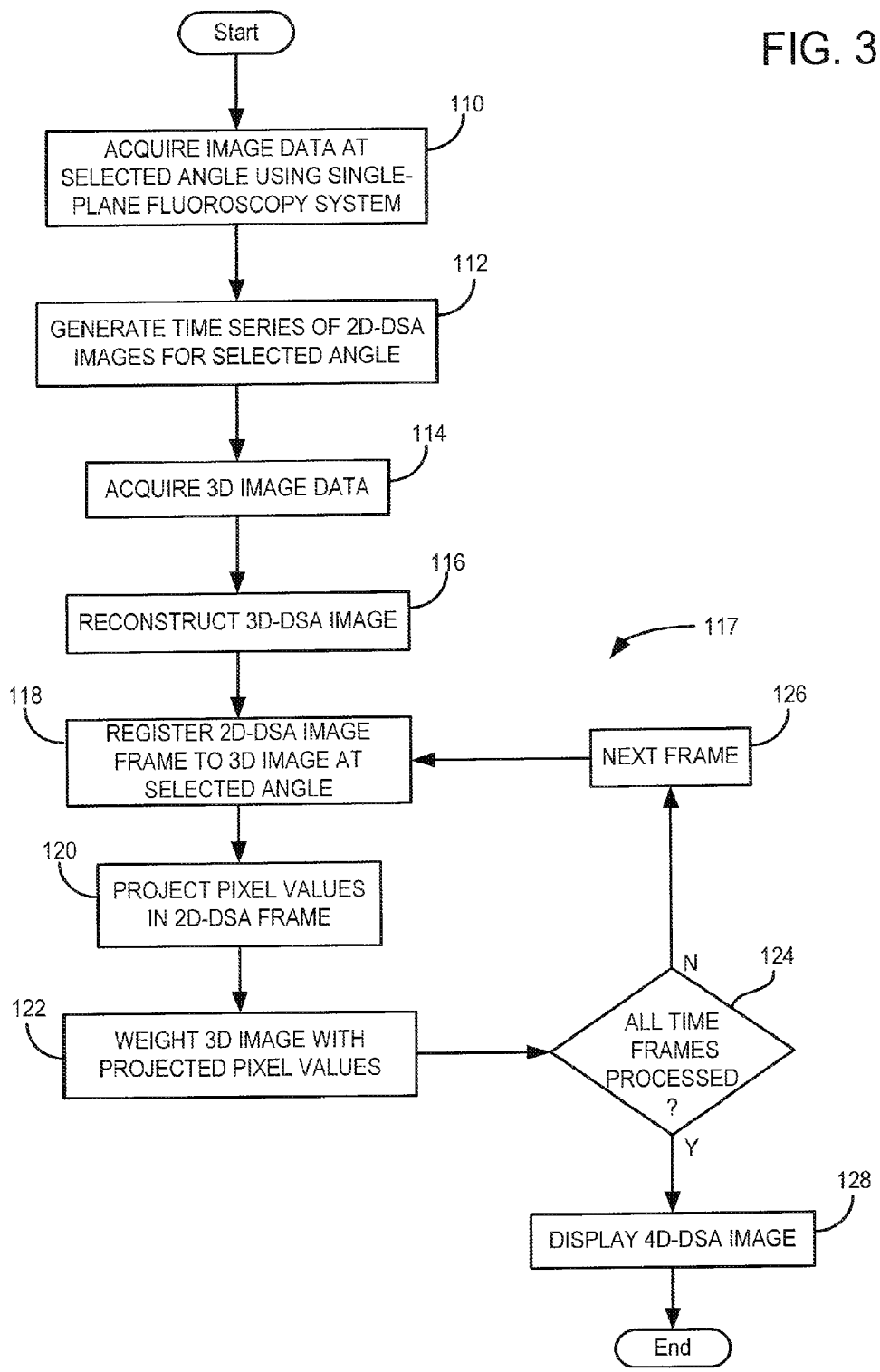
FIG. 3 is a flowchart setting forth the steps for producing a 4D-DSA image from time-resolved 2D images acquired using a single plane x-ray system in accordance with the present invention.

Referring to FIG. 3, a more specific implementation of the above method can be employed to produce a 4D-DSA image of a subject using a single-plane x-ray system in combination with a rotational x-ray system or CT system. This particular method begins at process block 110, when time-resolved image data from a ROI in the subject is acquired using the single-plane system following the administration of a contrast agent to the subject. Using the above-discussed DSA techniques, a time-series of 2D-DSA images at the selected angle is generated at process block 112. These 2D-DSA images depict the contrast agent passing through and enhancing arterial structures in the ROI. The 2D-DSA images are substantially free of signal from non-vascular structures, as well as signal from venous structures can be excluded due to the high temporal resolution of the 2D acquisition. At process 114, a separate scan is performed following a second administration of contrast agent to the subject using either the rotational fluoroscopy system or CT system to acquire 3D image data from the ROI. A 3D-DSA image is reconstructed at process block 116 from the acquired 3D image data. Typically, vascular structures in the 3D-DSA image are substantially opacified due to the use of contrast agent and the time necessary for data acquisition.

Figure 4:
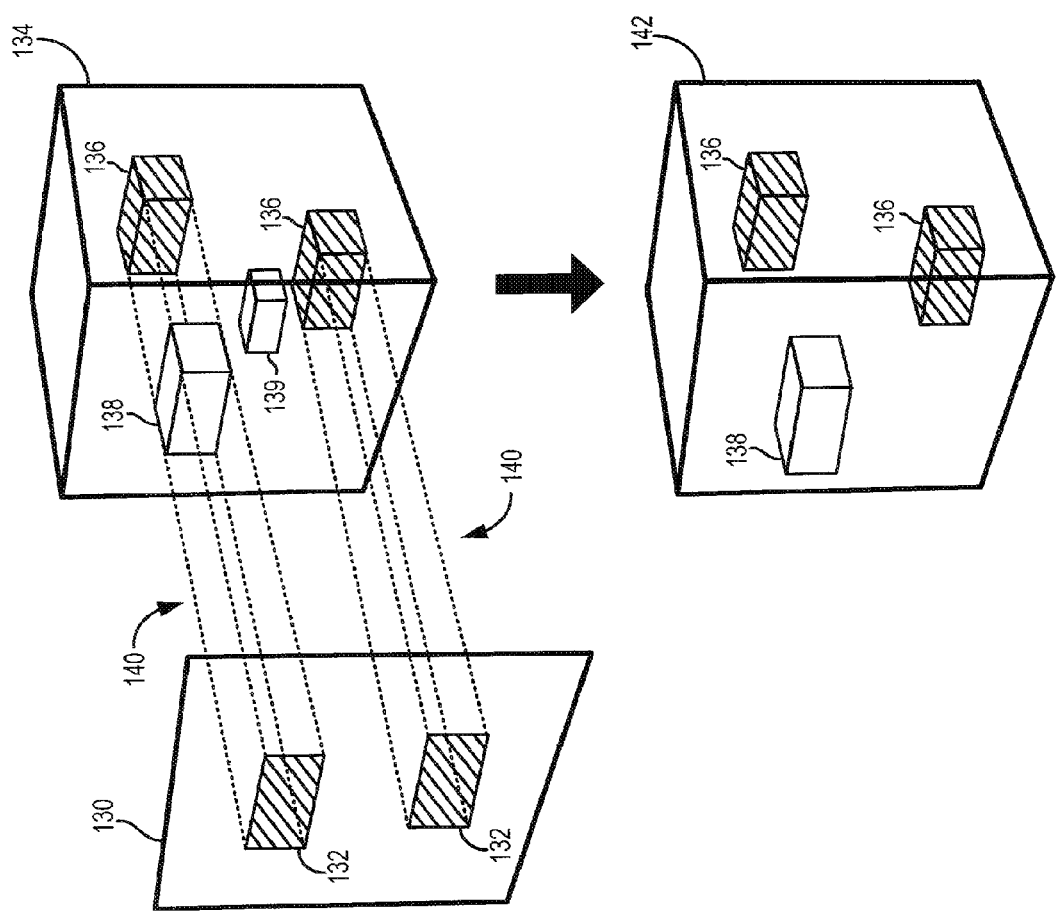
FIG. 4 schematically depicts the selective combination of a 3D image with a 2D-DSA image frame acquired using a single plane x-ray system in accordance with the present invention.

Referring now to FIGS. 3 and 4, the images produced thus far can now be selectively combined with the steps indicated generally at 117 to produce a 4D-DSA image with the detailed 3D resolution of the 3D-DSA image and the temporal resolution of the time-series of 2D-DSA images. In the exemplary depiction of the selective combination process provided in FIG. 4, a single frame of the time-series of 2D-DSA images 130 includes two image regions having arterial signal 132, while the 3D-DSA image 134 includes both arterial signal 136 and venous signal 138 and 139. At process block 118, a frame of the 2D-DSA image 130 is registered to the 3D-DSA image 132 at the selected angle and, at process block 120, the values of the pixels in the 2D-DSA frame are projected along a line passing through each respective pixel in a direction perpendicular to the plane of the 2D-DSA frame. The projection of pixels with arterial signal 132 into the 3D-DSA image is indicated generally at 140. For simplicity, the projection of pixels in the 2D-DSA frame with no contrast is not shown. At process block 122, the 3D-DSA image 134 is weighted by the values projected from the 2D-DSA frame 130 to produce the 4D-DSA image 142. Typically, this includes multiplying the projected values with the voxels of the 3D image that they intersect. The weighting process results in the preservation of the arterial signal 136 and the exclusion, or "zeroing-out," of undesired venous signal 139 in the 4D-DSA image. In addition, the intensity value of the arterial signal 132 in the 2D-DSA frame is imparted into the 3D arterial signal volume 136, thereby allowing the changes in arterial signal over time captured by the 2D-DSA images to be characterized in the 4D-DSA image. At decision block 124, if all of the frames have yet to be processed, the process moves to the next frame of the time-series of 2D-DSA images at process block 126 and repeats the selective combination process 117. This cycle continues until, at decision block 126, it is determined that a 4D-DSA image has been generated for all relevant time frames. The 4D-DSA image can thus be displayed at process block 128.

The venous signal 138 preserved in the 4D-DSA image 142 illustrates a potential problem when generating 4D images using only a single time-series of 2D images acquired at a single angle. Signal from desired structures, such as the arterial signal 132, can inadvertently be deposited in 3D voxels representing undesired structures, such as the venous region 138. The unwanted structures can thus be preserved in the 4D image as "shadow artifacts" when their signal lies along the projected values of a desired structure in a dimension inadequately characterized by the time-series of 2D images. This can result, for example, in a 4D-DSA image in which desired arterial structures are obscured by undesired venous structures for some time frames. However, this will cause a temporary anomaly in the contrast vs. time course for the vein. If the time frames of the 4D-DSA image are analyzed, this anomaly can be recognized as inconsistent with the general waveform of the vein and the vein can be suppressed in the time frame where the projected arterial signal is strong. Accordingly, temporal parameters such as mean transit time (MTT) or time-to-fractional-peak can be calculated for each voxel and this information can be used to clean up shadow artifacts. To assist an operator in identifying shadow artifacts and temporal irregularities, the temporal parameters can be color-coded and superimposed on the 4D-DSA image displayed at process block 128. The temporal parameters can also be exploited to infer information related to potential diffusion abnormalities in the absence of direct perfusion information from parenchymal signal.

Figure 5:
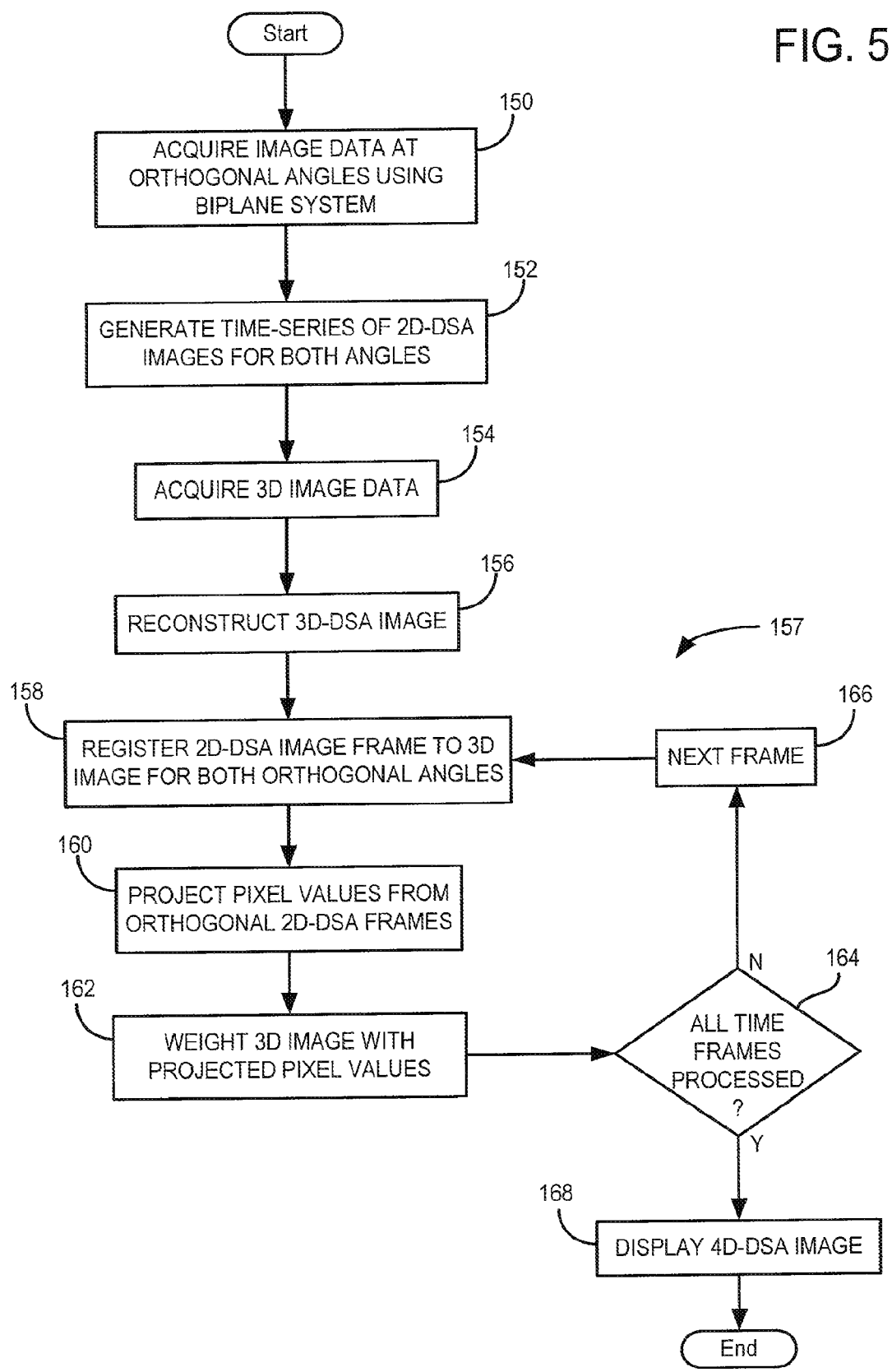
FIG. 5 is a flowchart setting forth the steps for producing a 4D-DSA image from a pair of orthogonal, time-resolved 2D images acquired using a biplane x-ray system in accordance with the present invention.

Referring to FIG. 5, a method for producing 4D-DSA images that are less prone to shadow artifacts begins at process block 150 with the acquisition of image data at a first angle and an orthogonal second angle using, for example, a biplane fluoroscopy system. The image data acquired at the orthogonal angles is then reconstructed at process block 152 to produce a first and second time-series of 2D-DSA images, that is, one for each orthogonal angle. For brevity, these two-time-series of 2D-DSA images may together be referred to as "orthogonal 2D-DSA images." At process block 154, a second scan is performed using, for example, a rotational fluoroscopy system or CT system to acquire 3D image data from the subject. At process block 156, the acquired 3D image data is reconstructed to produce a 3D-DSA image of the subject that is substantially without temporal resolution. Again, both the 3D-DSA and orthogonal 2D-DSA images are acquired while a contrast agent is administered to the subject and signal corresponding to non-vascular structures is removed by subtracting out a mask image.

Figure 6:
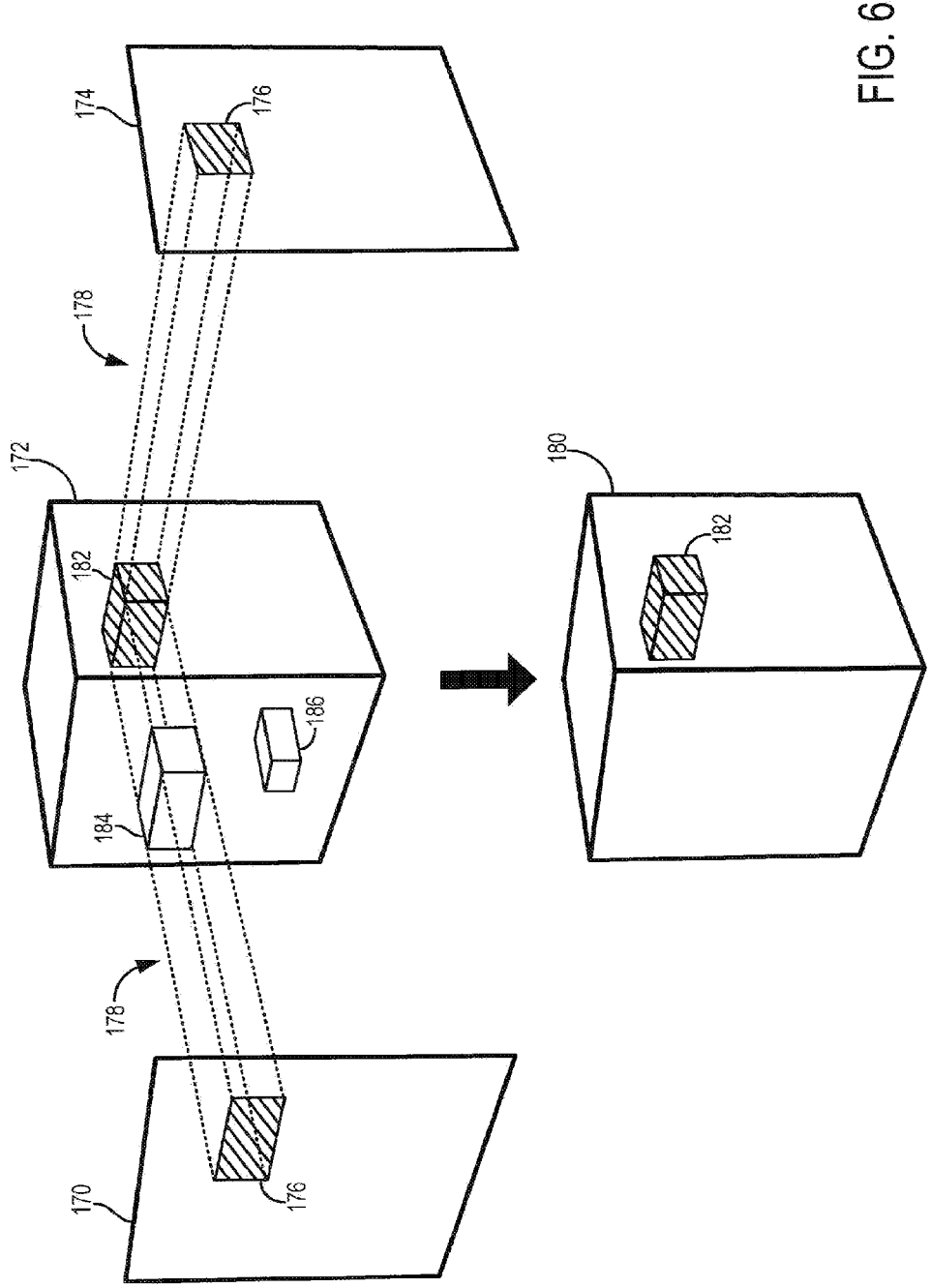
FIG. 6 schematically depicts the selective combination of a 3D image with a two orthogonal 2D-DSA image frames acquired using a biplane x-ray system in accordance with the present invention.

Referring now to FIGS. 5 and 6, the process of selectively combining the orthogonal 2D-DSA images and the 3D-DSA image is indicated generally at 157 and is depicted schematically in FIG. 6. Specifically, a frame of the first time-series of 2D-DSA images 170 is registered to the 3D-DSA image 172 at the first angle and a frame of the second time-series of 2D-DSA images 174 is registered to the 3D-DSA image 172 at the second angle. The two time-series of 2D-DSA images are thus registered into the 3D space of the 3D-DSA image at orthogonal angles. At process block 160, the pixel intensities of each orthogonal 2D-DSA frame are projected into the 3D-DSA image. The projection of arterial signal 176, that is, pixels having contrast, is indicated generally at 178. For simplicity, the projections from pixels having no contrast are not depicted in FIG. 6. At process block 162, the projected values from both of the orthogonal 2D-DSA frames are used to weight the 3D-DSA image and thus produce the 4D-DSA frame 180. Regions of arterial signal 182 from the 3D-DSA image are thus carried over to the 4D-DSA image, though their intensities are generally modulated based on the projected intensity of the corresponding arterial signal 176 in both 2D-DSA frames. Regions of venous signal 184 and 186 in the 3D-DSA image are excluded, or "zeroed out," from the 4D-DSA image since there is no corresponding projected signal from both 2D-DSA frames. The removal of arterial signal 184 is notable, especially compared to the above-described single-plane 4D-DSA method. Even though the venous signal 184 lies along a projection from pixels with contrast in the 2D-DSA frame 170, it does not lie along a projection from pixels with contrast in the, orthogonal, 2D-DSA frame 174. Accordingly, the venous signal 184 is zeroed out by projections from pixels without contrast (not shown) in the 2D-DSA frame 174.

At decision block 164, if all the frames have not been processed, the process moves to the next time frame of both time-series of 2D-DSA images at process block 166 and the selective combination process 157 is repeated so that orthogonal projections weight the 3D-DSA image and enable formation of frames of the 4D-DSA image. This cycle continues until, at decision block 164, it is determined that the 4D-DSA image has been rendered for all relevant time frames. Following its completion, the 4D-DSA image can displayed at process block 128.

Figure 7:
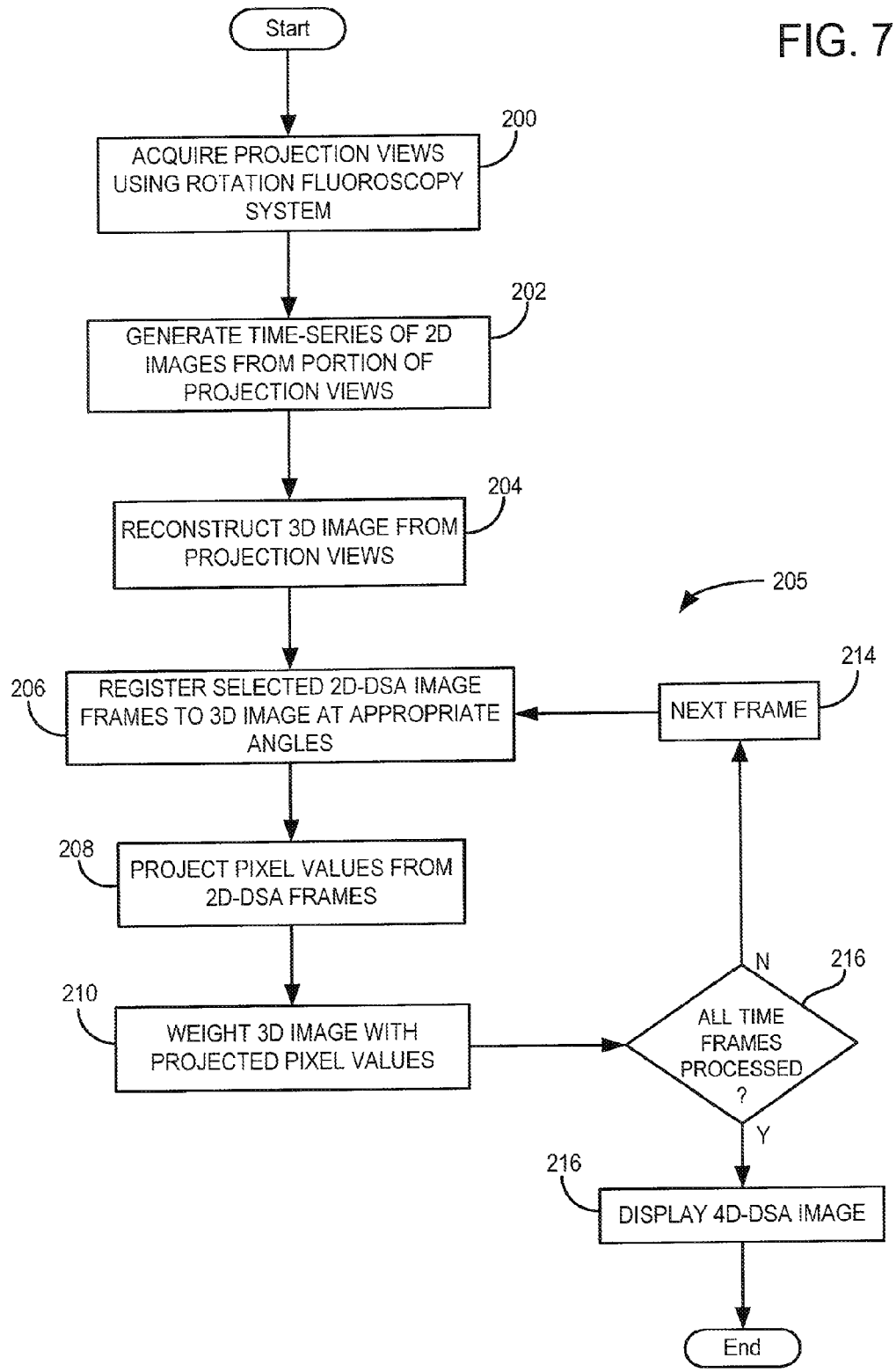
FIG. 7 is a flowchart setting forth the steps for producing a 4D-DSA image from a single set of projections views acquired using a rotational x-ray system or CT system in accordance with the present invention.

Referring to FIG. 7, while the above-described methods for generating 4D-DSA images generally involve two separate scans using two separate imaging systems and contrast agent injections, the general method of the present invention, which was outlined with respect to FIG. 2, can be performed on a single medical imaging system using a single contrast agent injection. Such a method begins at process block 200 with the rotational acquisition of projection views of a ROI in a subject using a rotational imaging system. A contrast agent is administered to the subject so that it passes through the ROI during a portion of the time period during which the acquisition is performed. At process block 202, a time-series of 2D-DSA images is generated from projection views acquired while contrast agent passed through the ROI. A 3D-DSA image of the subject substantially without temporal resolution is reconstructed from substantially all of the acquired projection views at process block 204. Because many of the projection views are acquired after the bolus of contrast agent has passed through the ROI, the region's vasculature is generally depicted as opacified in this 3D-DSA image.

The 2D-DSA images and the 3D-DSA image are selectively combined to produce a 4D-DSA image, as indicated generally at 205. Because a rotational acquisition is used, the time-series of 2D-DSA images includes projection images, or "projections," each acquired at a given time and angle. Accordingly, a single time frame of the 4D-DSA image can be produced by selectively combining the 3D-DSA image with a set of selected projections acquired over a given angular range $\Delta\Theta$, so long as the time difference between each of selected projections is relatively small. For example, for an acquisition in which 150 projection views are acquired over a 5 second time period, consecutive projection images are separated by 1 degree and 30 ms. A frame of a 4D-DSA image with a 0.2 second temporal resolution can be thus be generated by selectively combining the 3D-DSA image with consecutive projection images acquired over 6 degree angular range.

Referring now to FIGS. 7 and 8, therefore, at process block 206 each projection in the set of selected projection images is registered with the 3D image at an appropriate angle. At process block 208, the pixel intensities in each of these projection images is projected into the 3D-DSA image. At process block 210, the projected pixel values are then used to weight the 3D-image, generally via multiplication, and generate a time frame of the 4D-DSA image. At decision block 212, if all frames have yet to be process, the method moves to the next set of selected projection views at process block 214, which correspond to the next time frame of the 4D-DSA image, and the selective combination process 205 is repeated. This cycle continues until, at decision block 212, it is determined that the 4D-DSA image has been rendered for all relevant time frames. Following its completion, the 4D-DSA image can displayed at process block 216. The formation of a 4D-DSA image frame 220 by selectively combining two registered projections images 222 and 224 and a 3D-DSA image without time dependence 226 is schematically depicted in FIG. 8. Projected arterial signal 228 from the projection images 222 and 224 weights arterial voxels 230 in the 3D-DSA image 226, while projected signal from pixels without contrast 232 nullifies venous voxels 234 in the 3D-DSA image 226. The resulting 4D-DSA image frame 220, thus, includes weighted arterial signal 236, but does not include undesired venous signal, despite the fact the venous voxels 234 and arterial voxels 230 of the 3D-DSA image are aligned for one of the projection images.

It should be noted that there are potential tradeoffs with this single rotational acquisition approach. The ability to effectively cancel venous structures using the multiplicative projection operation increases with $\Delta\Theta$. However, temporal resolution decreases as $\Delta\Theta$ increases. In additional, temporal resolution may be degraded relative to the above-described single-plane and biplane methods, since the contrast bolus may not be made as compact during the rotation because of the potential for artifacts related to inconsistent projection weighting from contrast variations. Accordingly, rotation acquisition settings may be changed to reach a desired balance of temporal resolution and artery/vein overlap ambiguity.

Time-resolved 3D images produced in accordance with the present invention have significantly improved spatial and temporal resolution over images produced using traditional methods and, thus, have great utility in the diagnosis, pre-treatment planning, and post-treatment assessment of complex vascular conditions. In addition, these images allow the implementation of time-resolved true 3D roadmaps for use in minimally invasive interventional procedures, thereby facilitating the improved manipulation of surgical devices in complex vasculature. In particular, the present invention allows the implementation of 4D fluoroscopy using real-time sequences of surgical device movement combined with spatially and temporally selectable roadmaps obtained from 4D-DSA images. For example, catheter information acquired via either single plane or biplane fluoroscopy can be embedded within 4D-DSA vascular time frames to permit viewing at an arbitrary angle without further gantry movement. Catheter information acquired via real-time single projection subtracted fluoroscopy can likewise be superimposed on 4D-DSA time frames that are registered at the gantry angle is adjusted.

Referring to FIG. 9, in the formation of a fluoroscopic image, it is important that the spatial resolution of the surgical device be maintained. This can differ from the formation of 4D-DSA time frames where time-resolved 2D-DSA time frames are convolved and used to get a local spatial estimate of temporal weighting. It is better to provide an unconvolved and isolated depiction of the surgical device information so that resolution is maintained, though it should be noted that the lack of convolution can encumber image registration. The formation of images suitable for proper magnification and registration between a moving surgical device, a catheter, and a 4D-DSA image frame is illustrated in FIG. 9. With the catheter mostly out of the field-of-view (FOV), fluoroscopic image 240 and 242 are obtained before and after contrast injection, respectively. These images are subtracted to define an image 244 of the vessel position in the fluoroscopic image series. The catheter is then advanced to obtain image 246, which is subtracted from 240 to form the catheter-only image 248 that is added to a selected 4D DSA frame 250 to form the 4D fluoroscopic mage 252. For comparison, in traditional fluoroscopy, a fluoroscopic image 254 is formed by subtracting the image 246 depicting the advanced catheter from the fluoroscopic image 242 obtained after contrast injection.

When embedding surgical device information acquired via biplane fluoroscopy in 4D-DSA images, the fluoroscopic images are acquired in orthogonal pairs and the above process can be performed for both images. In this case, objects in the resulting 4D fluoroscopic image 252 are registered with the single projection bi-plane images 240-246. Generally, the first step in the registration process is the application of block matching with variable magnification and position in order to register images 244 and 250 in lateral and coronal views. Then the catheter image 248 is added in to form the 4D fluoroscopic image 252, which is registered to the traditional fluoroscopic image 254 using block matching. A range of horizontal and vertical magnifications are typically searched during the registration procedure. For each magnification a spatial displaced block search can be used to minimize the sum of absolute differences between 4D DSA time frames and displaced fluoroscopic time frames and the magnification and translation that minimizes this sum may be chosen for registering the images. To accelerate the search procedure in fluoroscopic dose reduction algorithms it is possible to employ an iterative block matching technique that initially uses large blocks and then proceeds to smaller blocks.

The formation of catheter image, such as image 248, can be noisy due to the multiplicative combination of noise from two biplane time-resolved images. Therefore, a noise reduction scheme may be implemented prior to the combination of the catheter image and the 4D-DSA time frame. For example, a spatially adaptive linear filter may be used so that in each element of an image sub-region matrix, the direction of the catheter is determined by calculating the sum of the pixel value within the block as a test object similar in size to the catheter is rotated through the block. The minimal sum is, thus, achieved when the test object has the same orientation as the catheter and a linear convolution filter can be applied along this direction to reduce catheter discontinuities caused by noise in acquired biplane images. Different grid sizes, test object rotation angles, and translation scheduling can be used depending on image quality and processing speed requirements. The size of the linear convolution kernel can also be varied to achieve a desired balance between noise and discontinuity reduction and potential errors in catheter tip localization. Following the application of this spatially adaptive linear filter, a motion adaptive integration of fluoroscopic image frames can also be used to reduce noise. Alternative spatially adaptive filters may also be used to improve the intelligibility of catheter images. For example, another approach is to scan the initial catheter images point by point and look at the direction in which the maximum linear sum over some number of pixels occurs. The linear filter can then operate in this direction, since it corresponds to the local orientation of the catheter. Depending on the size of the convolution kernel, the search grid can be adjusted and multiple convolutions of the same catheter segment may be performed.

A distinction should be considered when comparing the relative noise properties of the fluoroscopic and DSA applications. In the case of generating 4D-DSA frames the anatomical details are supplied by the 3D-image, for example, as acquired by a rotational DSA examination, and the acquisition's individual projections or independently acquired 2D-DSA images provide a local spatially averaged estimate of how much the vasculature is present at each point in time. This spatial average reduces noise and it is not required that the spatial information of the time dependent frames be maintained. In contrast, it is beneficial to maintain the spatial resolution of the fluoroscopic images depicting the catheter so that there is no intrinsic noise averaging except for that imposed by the filters discussed above. It should also be noted that the computation time for generating 4D-DSA frames and generating 4D fluoroscopic images can differ significantly. It is not necessary to reconstruct 4D-DSA images in real time, whereas fluoroscopic images should be subjected to registration and noise averaging algorithms in real time with minimal latency.

With a biplane fluoroscopy system, surgical device information from orthogonal time-resolved image series is typically multiplied into a binarized version of the 3D rotational DSA voxels. Following projection from one dimension there is uniform deposition of surgical device signal across the vasculature depicted in the 3D rotational DSA voxels. The intersection of this signal with corresponding signal from the orthogonal view carves out the 3D catheter voxels. A single plane system cannot acquire this additional orthogonal view. However, an alternative is to deposit all of the catheter signal in the center of the vessels depicted in a binary rotational DSA display. The maximum intensity projection (MIP) through this data set at any point of time can then be superimposed on the MIP through a corresponding 4D-DSA time frame, thus resulting in images that are roughly equivalent to those produced using biplane methods and the advancement of the surgical device is well represented. This approach of constraining the catheter to the center of a vessel in the direction not captured by the single plane acquisition does not involve any significant disadvantage compared to traditional fluoroscopic views, in which catheter position is unknown in one direction.

For systems without biplane capabilities, the flexibility of roadmap selection provided by the 4D DSA time frames can additionally be exploited by superimposing the single plane fluoroscopy on the MIP of the 4D DSA time frame taken at a given gantry angle. This involves registration at just the current projection for each gantry angle. Because it is not necessary that orthogonal surgical device views intersect to form a 3D spatial catheter volume, registration is of less importance and the full image quality of live fluoroscopy is essentially maintained. It is contemplated that this gantry rotation mode offers improved SNR, since it does not involve the multiplicative noise effects that occur when embedding biplane surgical device information into a 4D-DSA image, as discussed above for establishing a 4D fluoroscopic volume without gantry rotation.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A system for producing a time-resolved three-dimensional image of a subject, the system comprising:
  a computer processor configured to:
    receive image data acquired from the subject using a single rotation of a rotational medical imaging system over a time period, wherein a single contrast agent injection is administered to the subject during a portion of the time period;
    generate a time-series of two-dimensional images from the image data, each of the two-dimensional images corresponding to a different time in the time period and a different angle relative to the subject, wherein each of the two-dimensional images comprises pixel intensity information;
    reconstruct a three-dimensional image without temporal resolution from the image data;
    determine, for each of a plurality of the two-dimensional images, voxel weightings in the three-dimensional image without temporal resolution by multiplying the voxels with the pixel intensity information of a two-dimensional image in the plurality; and
    produce a time-resolved three-dimensional image of the subject by selectively combining the three-dimensional image substantially without temporal resolution and the time-series of two-dimensional images, the voxel weightings being used to nullify one or more voxels from the three-dimensional image without temporal resolution to produce the time-resolved three-dimensional image.

2. The system of claim 1, wherein the nullified voxels in the time-resolved three-dimensional image correspond to undesired vascular structures.

3. The system of claim 2, wherein at least one of the nullified voxels corresponding to an undesired vascular structure is nullified by the voxel having different weightings from one or more of the two-dimensional images at different angles.

4. The system of claim 3, wherein the computer processor is further configured to remove shadowing artifacts from the time-resolved three-dimensional image based on a temporal parameter associated with each voxel of the time-resolved three-dimensional image comprising at least one of a mean transit time (MTT) or time to fractional peak value.

5. The system of claim 4, wherein the computer processor is further configured to superimpose a color coded display of the temporal parameter on at least one of the time-resolved three-dimensional image and a blood volume image generated from the three-dimensional image substantially without temporal resolution.

6. The system of claim 1, wherein the computer processor is further configured to generate a roadmap for an interventional procedure based on the time-resolved three-dimensional image of the subject.

7. The system of claim 6, wherein the computer processor is further configured to embed real-time surgical device information within at least one selected time frame of the time-resolved three-dimensional image of the subject.

8. The system of claim 7, wherein the computer processor is further configured to embed surgical device information acquired at a first and second angle using a biplane fluoroscopy system within corresponding angles of the time-resolved three-dimensional image of the subject.

9. The system of claim 8, wherein the computer processor is further configured to embed:
  surgical device information acquired at a first angle using a single-plane fluoroscopy system within a corresponding angle of the time-resolved three-dimensional image to produce a hybrid data set, wherein along a second angle that is thirty to ninety degrees relative to the first angle surgical device information is embedded within a center of vessels depicted in the time-resolved three-dimensional image; and
  superimpose a maximum intensity projection (MIP) through the hybrid data set on a MIP through the time-resolved three-dimensional image subject at a corresponding angle.

10. A non-transitory computer-readable medium having computer-readable instructions stored thereon that when executed by a computer system cause the computer system to perform a method, the method comprising:
  receiving time-resolved image data acquired from a region-of-interest (ROI) in the subject in a first acquisition performed over a time period prior to and during which a bolus of contrast agent passes through the ROI;
  generating a time-series of two-dimensional images from image data acquired in the first acquisition, each of the two-dimensional images corresponding to a different time in the time period and a different angle relative to the subject, wherein each of the two-dimensional images comprises pixel intensity information;
  receiving image data acquired from the ROI in a second acquisition;

reconstruct a three-dimensional image substantially without temporal resolution from the image data acquired in the second acquisition;

determining, for each of a plurality of the two-dimensional images, voxel weightings in the three-dimensional image without temporal resolution by multiplying the voxels with the pixel intensity information of a two-dimensional image in the plurality; and producing a time-resolved three-dimensional image of the subject by selectively combining the time-series of two-dimensional images and the three-dimensional image substantially without temporal resolution, the voxel weightings being used to nullify one or more voxels from the three-dimensional image without temporal resolution to produce the time-resolved three-dimensional image.

11. The computer-readable medium of claim 10, wherein the method further comprises:

registering the reconstructed three-dimensional image substantially without temporal resolution to the time-series of two-dimensional images; and projecting a value of each pixel in the time-series of two-dimensional images along a line extending through each respective pixel in a direction perpendicular to a plane of the time-series of two-dimensional images.

12. The computer-readable medium of claim 11, wherein the nullified voxels in the time-resolved three-dimensional image correspond to undesired vascular structures; and wherein the nullified voxels in the time-resolved three-dimensional image correspond to undesired vascular structures in the ROI.

13. The computer-readable medium of claim 10, wherein the method further comprises:

receiving time-resolved two-dimensional image data acquired at a first angle and a second angle between thirty and ninety degrees relative to the first angle using a biplane fluoroscopy system; and reconstructing a first and second time-series of two-dimensional images from the image data acquired at the first and second angles, respectively.

14. The computer-readable medium of claim 10, wherein the image data acquired in the second acquisition is acquired using a rotational x-ray system following an administration of a contrast agent using at least one of intravenous injection and intra-arterial injection.

15. The computer-readable medium of claim 10, wherein the method further comprises generating a roadmap for an interventional procedure based on the time-resolved three-dimensional image of the subject.

16. A system for producing a time-resolved three-dimensional image of a subject, the system comprising:

a computer processor configured to:

receive projection views of a region-of-interest (ROI) in the subject acquire over a selected time period using a single rotational acquisition, wherein a single bolus of contrast agent passes through the ROI during a portion of the selected time period;

generate a time-series of two-dimensional images of the ROI from projection views acquired during the portion of the selected time period during which the bolus of contrast agent passes through the ROI, each of the two-dimensional images corresponding to a different time in the time period and a different angle relative to the subject, wherein each of the two-dimensional images comprises pixel intensity information;

reconstruct a three-dimensional image of the ROI substantially without temporal resolution from substantially all of the acquired projection views;

determine, for each of a plurality of the two-dimensional images, voxel weightings in the three-dimensional image without temporal resolution by multiplying the voxels with the pixel intensity information of a two-dimensional image in the plurality; and produce the time-resolved three-dimensional image of the subject by selectively combining the time-series of two-dimensional images and the three-dimensional image without temporal resolution, the voxel weightings being used to nullify one or more voxels from the three-dimensional image without temporal resolution to produce the time-resolved three-dimensional image.

17. The system of claim 16, wherein the computer processor is further configured to:

register the reconstructed three-dimensional image substantially without temporal resolution to the time-series of two-dimensional images; and project a value of each pixel in the time-series of two-dimensional images along a line extending through each respective pixel in a direction perpendicular to a plane of the time-series of two-dimensional images.

18. The system of claim 17, wherein the nullified voxels in the time-resolved three-dimensional image corresponding to undesired vascular structures in the ROI.

19. The system of claim 16, wherein the computer processor is configured to remove non-vascular structures from the time-series of two-dimensional images and the three-dimensional image substantially without temporal resolution by subtracting image data acquired from the ROI prior to passage of the contrast agent bolus through the ROI from the acquired projection views.

20. The system of claim 16, wherein the projection views acquired during the portion of the selected time period during which the bolus of contrast agent passes through the ROI are acquired over a limited angular range of the rotational acquisition.

* * * * *